United States Patent [19]

Charm

[11] 4,239,852

[45] Dec. 16, 1980

[54] ANTIBIOTIC DETECTION METHOD

[75] Inventor: Stanley E. Charm, Newton, Mass.

[73] Assignee: Penicillin Assays, Inc., Boston, Mass.

[21] Appl. No.: 914,414

[22] Filed: Jun. 12, 1978

Related U.S. Application Data

[63] Continuation-in-part of Ser. No. 853,541, Nov. 21, 1977, abandoned.

[51] Int. Cl.$^2$ ............................................. G01N 31/14
[52] U.S. Cl. ............................................. 435/32; 424/1
[58] Field of Search ................. 195/103.5 A, 103.5 K; 435/32; 424/1

[56] References Cited

U.S. PATENT DOCUMENTS

| | | | |
|---|---|---|---|
| 3,673,410 | 6/1972 | Waite et al. | 424/1 X |
| 3,817,837 | 6/1974 | Rubenstein et al. | 195/103.5 R |

OTHER PUBLICATIONS

Edwards et al., Journal of Bacteriology, Aug. 1969 pp. 459–462.
Blumberg et al., Bacteriological Reviews, vol. 38, No. 3, pp. 291–335 (Sep. 1974).
Spratt, Eur. J. Biochem. vol. 72, pp. 341–352 (1977).

*Primary Examiner*—Lionel M. Shapiro
*Attorney, Agent, or Firm*—Kenway & Jenney

[57] ABSTRACT

A process for rapidly detecting as little as 0.001 I.U. ml of antibiotic in a sample of liquid such as milk. The process comprises the steps of incubating the sample together with a tagged antibiotic or antibiotic precursor and antibiotic sensitive cells under conditions which allow antibiotic molecules to attach to receptor sites in or on the cells, separating the cells with immobilized antibiotic from the remainder of the reaction mixture, and determining the quantity of tagged antibiotic on the cells. The amount of tagged antibiotic on the cells is a function of the quantity of antibiotic present in the sample. The process is well suited for detecting penicillin-type antibiotics and may be practiced using peroxidase-tagged 6-amino penicillanic acid and sonicated, penicillin supersensitive *Bacillus stearothermophilus* immobilized on a support.

17 Claims, 2 Drawing Figures

ANTIBIOTIC DETECTION METHOD

REFERENCE TO RELATED APPLICATIONS

This application is a continuation-in-part of copending U.S. application Ser. No. 853,541, filed Nov. 21, 1977, entitled Antibiotic Detection Method, now abandoned.

BACKGROUND OF THE INVENTION

This invention relates to a rapid, sensitive method for detecting the presence of antibiotics in liquids such as milk, body fluids, meat extracts, and fermentation broths.

The ability to detect small concentrations of antibiotics in liquids is important in various situations. One example is the food industry where the use of antibiotics in the treatment of animals which produce food stuffs has created a need for a rapid, accurate test method which can be used in the field by bulk food handlers and the like. Because penicillins are used to treat mastitis in dairy cattle, and because the Food and Drug Administration restricts the penicillin content of milk, antibiotic detection methods suitable for rapidly and accurately screening milk are particularly important. Thus, the growing medical concern about ingestion of small amounts of antibiotics by humans is directing attention to the incidence of penicillin in milk at levels in the range of 0.010–0.050 I.U./ml or greater and to simple screening methods for detecting such minute quantities of penicillin and other antibiotics.

At the present time, there are a variety of known antibiotic detection procedures. Most of these involve microbiological techniques wherein the presence or absence of penicillin or other antibiotic is determined by observing the inhibition of growth of antibiotic sensitive microorganisms in the pesence of the test sample. Formerly, such procedures required incubation times of four hours or more, but by employing microorganism strains "supersensitive" to antibiotics, the time required to perform the assays has been reduced to between 2 and 2½ hours.

Other antibiotic detection techniques exploit various other unique properties of the antibiotic or class of antibiotics to be detected as a test basis. Thus, in *Immobilized Enzyme-Based Flowing-Stream Analyzer for Measurement of Penicillin in Fermentation Broths*, J. F. Rusling et al., Analytical Chemistry, Vol. 48, p. 1211, (July, 1976), a test based on the enzymatic hydrolysis of penicillin with an immobilized $\beta$ lactamase derivative is disclosed. *Simple Ultrasensitive Test for Detecting Penicillin in Milk*, J. M. A. Palmer et al., J. Dairy Science, Vol. 50, p. 1390, discloses a penicillin detection method based on the growth of *Bacillus subtilis* spores on nutrient-spore-dye paper discs residing in a small sample of milk exposed to the air. As the water content of the milk evaporates, penicillin concentration, if any, increases and induces a color change in the dye which is indicative of concentration. U.S. Pat. No. 3,586,483 to J. G. Heider et al. discloses a method of detecting tetracycline antibiotics in fluids by absorbing the fluid on an absorbent strip containing a complexing metal which forms a fluorescent metal complex with the antibiotic, and by observing the fluorescence of the metal complex under ultraviolet light.

The foregoing and other available detection techniques vary widely with respect to their sensitivity and speed. It is believed that no presently available test is capable of detecting as little of 0.01 I.U. of penicillin per milliliter (6 ng/ml) in less than an hour. If such a test were available, it would become economical to rapidly and reliably determine, for example, whether milk sampled in the field from relatively small batches contained antibiotic concentrations in excess of Food and Drug Administration standards.

SUMMARY OF THE INVENTION

The instant invention provides a novel procedure for detecting the presence of antibiotics in liquids. Certain embodiments of the invention are ideally suited for screening milk for penicillin type antibiotics, and the invention will be described in detail with reference to this application. However, in view of the description which follows, it will be apparent that the invention may be used to assay body fluids, meat extracts, fermentation broths and the like for a variety of antibiotic drugs. The outstanding advantage of the process of the invention is that it is capable of detecting very small antibiotic concentrations, e.g., 0.001 I.U./ml of penicillin, and can do so rapidly, e.g., in less than 10 minutes.

In its broadest aspects, the process of the invention comprises the steps of incubating the sample with cells, or in some cases, cellular subunits, of an antibiotic sensitive microorganism under conditions to allow antibiotic molecules that may be present in the sample to attach to receptor sites associated with the cells, incubating the cell-sample mixture with a tagged antibiotic or antibiotic precursor under the same conditions, separating the cells from the liquid portion of the reaction mixture, determining the amount of tagged antibiotic present either in association with the separated cells or the remaining liquid, and comparing the determination to a standard. If antibiotic molecules were present in the sample, then the tagged and untagged molecules both seek to attach themselves onto a finite number of receptor sites on the cells or cellular subunits, and the amount of tagged antibiotic which becomes immobilized is inversely proportional to the concentration of antibiotic in the test sample. Similarly, the amount of tagged antibiotic which remains in the liquid phase will be a function of original antibiotic concentration.

The surprising sensitivity and speed of the test is believed to be a consequence of both the high binding constant characteristic of the attraction between antibiotic molecules and receptor sites on cell walls or other subcellular structures of antibiotic sensitive organisms, and the specificity of antibiotic molecules for their sites of action on such organisms. For example, the binding constant for penicillins with receptor sites on gram positive cells is orders of magnitude greater than the binding constant for the antigen-antibody immunochemical reaction on which analogous detection techniques (immunoassays) have been based.

In an important embodiment of the process of the invention, in the interest of providing a rapid test suitable for use in screening milk, a single incubation is conducted involving the antibiotic sensitive microorganism, the sample to be tested, and the tagged antibiotic or antibiotic precursor, and the separation step is effected by centrifugation. Both the speed and sensitivity of the assay are promoted by employing cell strains which are supersensitive to a class of antibiotics or specific antibiotic to be detected. Extending this concept one step further, the preferred antibiotic sensitive microorganisms are strains having a temperature of optimum growth above about 50° C. In this situation, the incubation can be conducted at relatively high temperatures and the kinetics of the antibiotic-receptor site organic reaction are enhanced. The preferred microorganism for conducting assays for β lactam antibiotics is *Bacillus stearothermophilus* (A.T.C.C. No. 10149 or 15952). However, various other antibiotic supersensitive cell strains can be used, and indeed, merely sensitive strains can be used if reduced sensitivity can be tolerated. Nonlimiting examples of suitable cell strains include certain mutants of *E. coli, Ps. aeruginosa, B. subtilis,* and *S. aureus.*

In embodiments of the process of the invention wherein speed is less important than sensitivity, the sample and cell culture are incubated for a time and the tagged antibiotic is added later. When employing sensitive microorganisms having the high optimum growth rate, it has been noted that sensitivity does not increase linearly with time and that incubations of greater than 15 minutes in duration should not be conducted.

In preferred embodiments of the invention, the tagged antibiotic is benzylpenicillin, or the antibiotic precursor 6 amino penicillanic acid, and the antibiotic to be detected is a β lactam antibiotic such as benzylpenicillin, cephalosporin, ampicillin, oxacillin, methicillin, cloxacillin, cephaloridine, and cephalothin. Other nonlimiting antibiotics which can be detected include erythromycin, lincomycin, actinomysin, vancomycin, bacitracin and aminoglycosides such as streptomycin, gentamycin, kanamycin, and neomycin. The process of the invention works exceptionally well with penicillin or penicillin-like antibiotics of the type which inhibit cell reproduction by attaching to sites on cell membranes to inhibit cell wall synthesis. However, antibiotics having other sites of action such as rifamycin and tetracyclines can also be detected. The tagged antibiotic can be tagged with a radioactive atom, an enzyme, enzyme inhibitor, or a conenzyme. Presently preferred tags include a $^{14}C$ incorporated in the structure of the antibiotic molecule, an $^{125}I$ atom attached to the antibiotic via reaction with, for example, tyrosine or suitable derivative thereof, and an enzyme such as peroxidase.

In another important embodiment of the invention, cell parts containing receptor sites are immobilized on an insoluble support, e.g., a cotton swab. This approach facilitates the separation step since, after incubation, the support can simply be removed from the liquid and washed. The need for a device capable of detecting radioactive decay products can be eliminated by tagging with an enzyme. In this case, the determination of the presence of the enzyme tag is made by incubating the support with an enzyme substrate solution capable of undergoing a detectable chemical change under the catalytic influence of the enzyme. A preferred system includes a peroxidase tag and a substrate solution comprising $H_2O_2$ and 4-amino antipyrine which changes color in the presence of peroxidase.

In accordance with another aspect of the invention, a test set for determining the presence of antibiotics in liquid samples is provided. The set has a quantity of concentration stabilized antibiotic sensitive (preferably supersensitive) cells, a quantity of tagged antibiotic or antibiotic precursor selected to have a high binding constant with the sites on the cells, and a standard against which the results of tests made with the reagents can be compared. In preferred embodiments, the test set includes freeze dried *Bacillus stearothermophilus,* the tagged antibiotic is benzylpenicillin tagged with a radioactive atom, e.g., $^{14}C$, and the standard is either a standard curve or at least one sample containing a known concentration of the antibiotic or class of antibiotics to be detected.

Another embodiment of the test set comprises a water insoluble support having penicillin super sensitive cells or cell membranes immobilized thereon, enzyme-tagged 6 amino-penicillanic acid, and an enzyme substrate solution capable of undergoing a color change in response to the catalytic influence of the enzyme tag. The enzyme tag can be peroxidase; the substrate solution comprises $H_2O_2$, phenol, and 4 amino antipyrine.

Accordingly, objects of the invention include the provision of an antibiotic detection technique which is capable of detecting a large number of different antibiotic drugs in a variety of liquid media, which can be adapted to be very rapid and acceptably sensitive, and which can be adapted to be slightly slower, but extraordinarily sensitive. Another object of the invention is to provide a fast antibiotic detection technique which can be conveniently conducted outside of the laboratory. Another object is to provide a test set suitable for determining the presence of as little as 1 ng/ml of antibiotic in a liquid sampled from materials such as milk, body fluids, meat residues, fermentation broths and the like. Yet another object is to provide a test set which enables the process of the invention to be conducted without a centrifuge or scintillation counter.

These and other objects and features of the invention will be apparent from the following detailed description of some important embodiments.

DESCRIPTION OF THE PREFERRED EMBODIMENT

Figure 1:
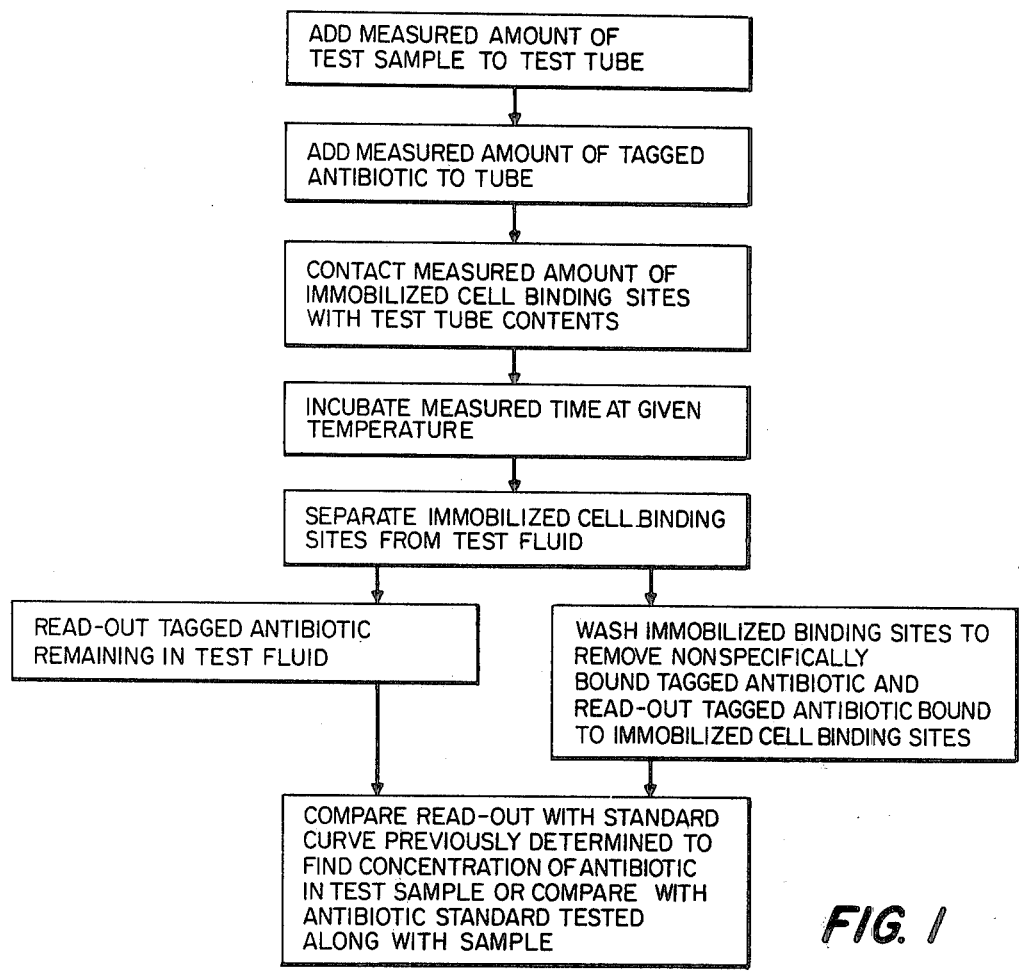
FIG. 1 is a flow chart illustrating the antibiotic detection process of the invention.

The process of the instant invention involves four basic steps: an incubation wherein antibiotic (if any) in the sample and tagged antibiotic become bound to antibiotic sensitive cells or cell subunits; a separation wherein the cells with bound antibiotic are isolated from the remainder of the system; a determination wherein an indication of the quantity of tagged antibiotic associated either with the cells or the separated liquid is obtained; and a comparison wherein the determination is compared with a standard. As the concentration of antibiotic in the test sample increases, fewer tagged antibiotic molecules will report in association with the cells (and more with the separated liquid).

By preparing a series of samples of known antibiotic concentration and treating them in accordance with the process of the invention, a standard curve of antibiotic concentration versus counts per minute (in case of radioactive tags) or the like can be produced. Assays of unknowns will give a quantitative indication of the antibiotic concentration if compared with such a curve. An indication of the presence of antibiotic in a sample may also be obtained by comparing the test sample read out of tagged antibiotic with the results of assays run in parallel with samples containing known amounts of antibiotic. If only the presence of antibiotic in concentrations above a certain maximum is sought, the necessary comparison step may be conducted indirectly. This is done by noting the read out associated with the test sample and comparing with a previously determined read out which has been correlated with the critical antibiotic concentration. This simple comparison is made possible by the standardization of reagents and procedure. Thus, the technician conducting the test inherently makes the comparison when he interprets the read out.

It is believed that the favorable sensitivity and speed characteristic of the assay are traceable to the typically high binding constants for the reactions between antibiotics and cells and to the specificity of the antibiotics for their sites of action. Thus, in the process of the invention, even extremely small quantities of antibiotic in a test sample rapidly become attached to receptor sites on the cell membrane or other location on the microorganism with which it is incubated. In this regard, it is well known that many antibiotics operate by attaching themselves onto certain cell locations, thereby preventing normal reproductive metabolism. For example, vancomycin, bacitracin, penicillins, and cephalosporins are known to inhibit cell reproduction by attaching to receptor sites on the cell membranes to thereby prevent cell wall synthesis. See, for example, *Correlation between Growth Inhibition and the Binding of Various Penicillins and Cephalosporins to Staphylococcus aureus*, J. R. Edwards et al., Journal of Bacteriology, August 1969, p. 459–462; and *The Actions of Penicillin and Other Antibiotics on Bacterial Cell Wall Synthesis*, J. L. Strominger, Hopkins Med. J., V. 133, p. 63 (1973). Other antibiotics have sites of action somewhat less accessible than the cell membrane, but nevertheless operate by attaching themselves to specific cell locations such as ribosomes or nucleic acids. Accordingly, in addition to the $\beta$ lactam antibiotics and other antibiotics set forth above, the process of the invention can detect erythromycin, lincomycin, actinomycin, and tetracyclines, as well as aminoglycosides such as streptomycin, neomycin, etc. These latter substances have various sites of action associated with the cells such as ribosomes and the like.

If tagged antibiotics are included in the incubation with the sample, then tagged and untagged molecules compete for the available receptor sites. If the tagged molecules are added after the sample has been incubated with the cells for a time, then tagged antibiotic molecules attach to remaining receptor sites. In either case, since by detecting the presence of tagged molecules immobilized on the cells one can obtain a measure of the extent of tagged antibiotic binding, an indirect measure of untagged molecule binding results since the amount of tagged antibiotic on the cells is a function of the quantity of antibiotic present in the sample.

Stated differently, the process of the invention depends on tagged antibiotic molecules and antibiotic which may be present in the sample seeking to react with a finite number of receptor sites on the cells either simultaneously or sequentially. Thus, a successful test may be conducted where the antibiotic to be detected and the tagged substance are the same antibiotic. However, any suitably tagged member of the class of antibiotics or related molecules such as antibiotic precursors or derivatives which attaches to the same group of receptor sites as the antibiotic to be detected can be used in the incubation. For example, any specific penicillin or cephalosporin antibiotic, suitably tagged, can be used to detect the same, any other, or a mixture of penicillins or cephalosporins. However, preferred antibiotics used for tagging are those members of a given class which have a high bonding constant such as benzylpenicillin (penicillin G), ampicillin, or cephalosporidine in the class of $\beta$ lactam antibiotics. An example of an antibiotic precursor in this class is 6 amino penicillanic acid; an example of a derivative is the reaction product of 6 amino penicillanic acid and tyrosine. As used below, the term "tagged antibiotic" or "tagged substance" includes tagged antibiotics, antibiotic precursors and derivatives, and other related substances which have an affinity for the sites of action of their parent antibiotic.

Regarding the nature of the tag, the state of the art is such that there are several types of tags available. Thus, the tagged antibiotic can contain a $^{14}C$, or $^{125}I$, or other radioactive atom detectable by a counter or the like, or any enzyme, enzyme inhibitor, (e.g. methotrexate) or coenzyme (e.g. NAD) which are detectable by subjecting the tagged antibiotic to a substrate solution which undergoes a detectable chemical reaction under the catalytic influence of the tag, or in which a reaction is inhibited. Excellent results have been obtained using radioactive tagged antibiotics, for example, $^{14}C$ tagged benzylpenicillin (penicillin G), which is now commercially available. Those skilled in the art will appreciate that in most cases a derivative to the antibiotic molecule must be synthesized in order to furnish a site of attachment for a radioactive iodine atom. Enzyme tags have also been used with success, and coenzymes such as dehydrogenase coenzymes can be employed. The presence of the enzyme tag is determined in a known manner using an enzyme substrate solution which, for example, changes color on exposure to the enzyme. The quantitative determination of the coenzyme is accomplished by subjecting the separated cells (or remaining liquid) to a solution containing a substrate which changes color when acted upon by an enzyme system, a critical component of which is the coenzyme. The other enzymes in the system are included in the solution.

Broadly, the cells which can be used in the process of the invention comprise any cell which is sensitive to the antibiotic to be detected. Thus, for example, any microorganism that is inhibited by penicillin could be used to detect pencillin type antibiotics. However, to improve sensitivity, it is much preferred to employ a microorganism which is "supersensitive" to the antibiotic to be detected. In recent years, many strains of cells supersensitive to either specific antibiotics or classes of antibiotics have become available. Examples of $\beta$ lactam sensitive microorganisms include *B. subtilis, B. megaterium, S. aureus, Ps. aeuginosa,* and certain mutants of *E. coli*. Most favorable results in terms of speed and sensitivity have been achieved using supersensitive microorganism strains which have an optimum temperature of growth generally in excess of about 50° C. The preferred microorganism in this regard is *Bacillus stearothermophilus* (A.T.C.C. No. 10149). *B. stearothermophilus* A.T.C.C. No. 15952 may also be used. Because the incubations can be conducted at high temperature with this type of microorganism, the rate of antibiotic binding is increased.

It should be noted that whole cells need not necessarily be used in the process of the invention. Thus, the cellular subunits on which the receptor sites are located, e.g., cell walls or membranes, ribosomes, bound enzymes, etc., may be used in place of the intact cells. For example, penicillin G is known to bind to and inhibit the action of D-alanine carboxypeptidase which is normally immobilized on cell membranes. However, methods are now available for the isolation of such enzymes, and these may be used in place of whole cells (see, *Purifica-* tion and Characterization of Thermophilic D-Alanine Carboxypeptidase from Membranes of B. stearothermophilus, R. Rogers et al., J. Biol. Chem. V. 249 p. (4863-4876). While separation of such subunits from the remainder of the reaction mixture may be difficult to accomplish quickly unless, as taught herein, the subunits are immobilized on an insoluble solid or the like, those skilled in the art will appreciate that the use of such materials is the equivalent of using whole cells. As used herein, the term "cell parts" accordingly refers to whole cells as well as cellular subunits such as cell membranes or other structures containing receptor sites.

The process of the invention can also be practiced using cell parts containing receptor sites immobilized on a suitable support such as a cotton swab, collagen matrix, polystyrene well or bead, polyacrylamide gel, or a small quantity of a shape retaining nutrient agar attached to a dip stick. In this situation, separation of the cells from the liquid components of the reaction mixture is greatly simplified and speeded up. When whole cells are used, a preferred method of separation is by centrifugation. However, other methods of separating the cells from the remainder of the reaction mixture, e.g., ultrafiltration, can be employed.

In view of the foregoing it will be appreciated that the test of the invention may be adapted to detect the presence of a variety of antibiotics or mixtures thereof in a number of different liquid media. A variety of tagged antibiotics and cells or cell subunits may be used, and either a qualitative or quantitative test may be designed. The invention will now be described with reference to specific, nonlimiting embodiments suitable for rapidly screening milk samples for the presence of as little as 0.001 I.U./ml of penicillin.

EXAMPLE 1

*Bacillus stearothermophilus* was grown in accordance with the following.

Medium:
Solution A
  Difco yeast extract: 2.58 kg
  Difco bactotryptone: 2.58 kg
  Sodium phosphate, dibasic: 1.54 kg
  Potassium phosphate, monobasic: 515 g
  Ammonium sulfate: 515 g
  Distilled water: 515 liters
Solution B
  Magnesium sulfate, anhydrous: 103 g
  Distilled water: 1.29 liters p0 Solution C
  Calcium chloride.2 $H_2O$: 12.9 g
  Manganese chloride: 0.52 g
  Distilled water: 1.29 liters
Solution D
  Glucose: 2.58 kg
  Distilled water: 12.9 liters
Conditions: 60° C., aeration, 10% inoculum
Growing time: 2.5 hours
Procedure:
Solution A is sterilized in the fermentor. Solution B is sterilized separately and 2.5 ml added to each liter of Solution A. The final concentration of magnesium sulfate in the medium is 0.2 g/liter. Solution C is sterilized separately and 2.5 ml added to each liter of Solution A. The final concentration in the medium is:
  calcium chloride.2 $H_2O$: 0.025 g/liter
  manganese chloride: 0.001 g/liter Solution D is sterilized separately and 25 ml added to each liter of Solution A. The final concentration of glucose in the medium is 5 g/liter.

The temperature of Solution A in the fermentor should be between 60°-65° C. Solutions B, C, and D are added with vigorous stirring of the fermentor. Slow addition of Solution C and vigorous stirring were necessary to prevent the formation of a precipitate. The complete medium has a pH of 6.9 without adjustment. Dow Corning B antifoam is added to give a concentration of 0.1%. Very vigorous aeration is required for growth of the organism.

When the fermentation is initiated, a carboy containing six liters of complete medium is inoculated with the contents of two one-liter Ehrlenmeyer flasks, each of which contains 150 ml of a culture grown overnight. When a reading of O.D. 0.150 (600 mu) is attained, the entire contents of the carboy are used to inoculate the 60 liter fermentor. When the solids are 0.03%, the 60 liter fermentor is used to inoculate the 530 liter fermentor.

The cells are washed twice with five volumes of 0.2 M $NH_4Cl$, pH 7.0, then twice with 10 volumes of a buffer containing 0.01 M magnesium acetate, 0.01 M mercaptoethanol, and 0.02 M Tris-HCl buffer, pH 7.8.

The cells were then centrifuged and after decanting the supernatant, were resuspended in a mixed solution of A, B, and C (above) and dispensed into vials. The contents of each vial can be freeze dried by known methods and stored at about 4° C. for extended periods of time. Freeze drying in the growth medium (minus glucose solution) preserves the maximum antibiotic binding activity of the cells. Such freeze dried cells constitute an ideal concentration stabilized source of cells for use in a test set.

The tagged antibiotic employed was benzylpenicillin containing a $^{14}C$ atom (150µ Curie/mg) and was purchased from Amersham Searle Co. This reagent can also be freeze dried for stability.

To obtain quantitative results and to act as a control, two or more liquid samples, one of which is known to be antibiotic free and the other of which contains a known quantity of the antibiotic to be detected, e.g., 0.01 unit per ml of penicillin, can be tested in parallel. These samples can also be freeze dried for stability. Any of the foregoing reagents can be reconstituted with distilled water or phosphate buffer having a slightly acidic pH. For penicillins, binding occurs optimally between pH 6.0-7.0. The stabilized cells, tagged antibiotic, and controls (or standard curve) constitute a test set suitable for conducting assays in accordance with the invention.

The reagents set forth above were used to prepare a standard curve and to test unknowns for the presence of penicillin. One standard curve was prepared by subjecting 12 1.0 ml milk samples containing known concentrations of benzylpenicillin (penicillin G) to an incubation with a (1) 100 ml sample of a B. stearothermophilus suspension (reconstituted from freeze dried material by adding 2.5 ml distilled water to a vial produced as set forth above) and (2) $^{14}C$ tagged benzylpenicillin (penicillin G) in sufficient quantity to give about 10,000 counts/minute. The incubation was conducted for three minutes in a dry bath incubator set at 90° C. The cells were then separated by centrifugation at 3,000 xg for two minutes. The supernatant was discarded, and the tube was rinsed with phosphate buffer without disturbing the cells. The cells were then transferred from the tube to a scintillation vial using scintillation fluid as a wash. This latter step may be eliminated and the tagged molecules directly detected if a $^{125}I$ tag is used. Results are set forth in table I below:

Table I

Standard Curve for Detection of Benzylpenicillin

| Sample No. | [Benzylpen] ng/ml | Counts/10 min. | Background Corrected Counts/10 min. | Average Counts/10 min. | $C/C_o$** |
|---|---|---|---|---|---|
| 1 | * | 331 | 84 | | |
| | | | | 102 | .007 |
| 2 | * | 367 | 120 | | |
| 3 | 0 | 15457 | 15210 | | |
| | | | | 15272.5 | 1.000 |
| 4 | 0 | 15582 | 15335 | | |
| 5 | 1.0 | 13165 | 12918 | | |
| | | | | 13019.5 | .853 |
| 6 | 1.0 | 13368 | 13121 | | |
| 7 | 5.0 | 9859 | 9612 | | |
| | | | | 10002. | .655 |
| 8 | 5.0 | 10639 | 10392 | | |
| 9 | 10 | 7615 | 7368 | | |
| | | | | 7699 | .504 |
| 10 | 10 | 8277 | 8030 | | |
| 11 | 50 | 4175 | 3920 | | |
| | | | | 4071 | .267 |
| 12 | 50 | 4461 | 4214 | | |

*20,000 units benzylpenicillin (penicillin G) added to sample.
**Counts of sample/counts of control (zero penicillin G present in sample).

Figure 2:
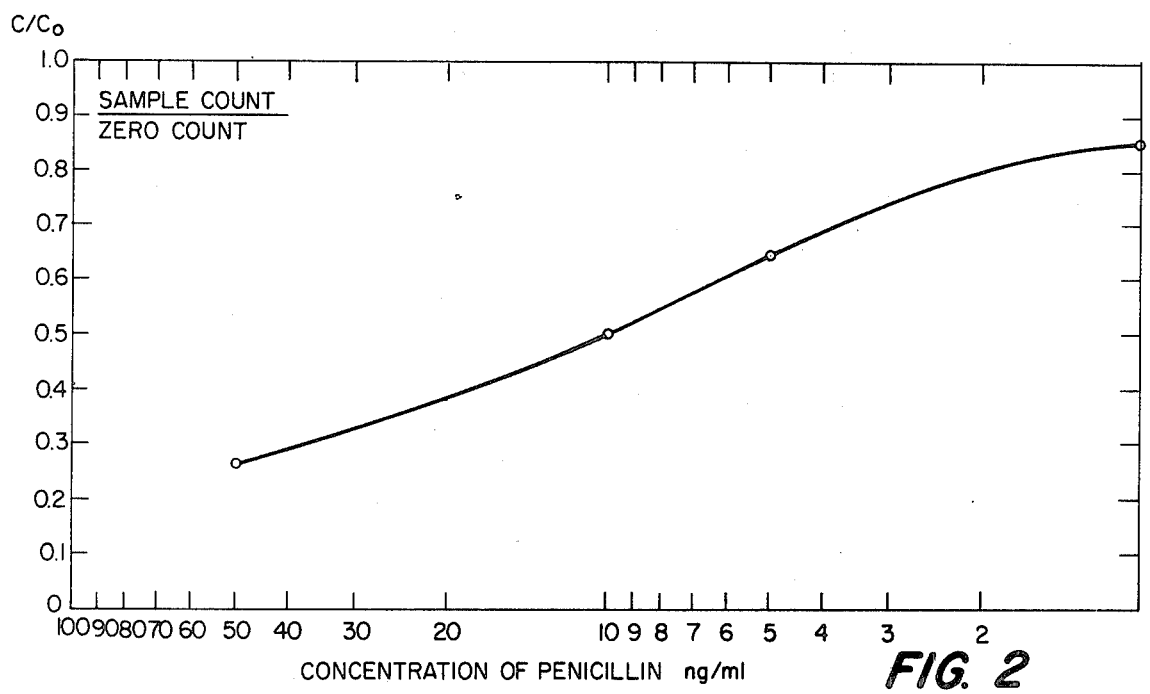
FIG. 2 is a standard curve for practice of the invention in the detection of benzylpenicillin.

As can be appreciated from the foregoing table, a significant and dramatic decrease in the count occurs as the amount of benzylpenicillin in the samples in increased from zero (3,4) to 10 ng/ml (9, 10). The data in Table I is graphically presented in FIG. 2, wherein penicillin concentration in ng/ml is plotted vs. sample count/zero count.

Using the foregoing table as a standard of comparison, tests were conducted on 20 milk samples prepared by a commercial milk processor. The procedure employed was identical to the procedure for preparing the standard curve set forth above except for the additional step of comparing the counts/minute obtained with the test samples with the curve and converting ng/ml of penicillin to I.U./ml (0.01 I.U./ml ≈ 6 ng). The results of these tests are set forth in table II below:

Table II

Comparison of Sensitivity of Microbiological Technique and Technique of the Invention Assay Results

| Sample No. | Known Penicillin Concentration IU/ml | Using Microbiological Technique (IU/ml) | Test Results (per ml) IU |
|---|---|---|---|
| 1 | .005 | — | .007 |
| 2 | .005 | — | .009 |
| 3 | .003 | — | .008 |
| 4 | .002 | — | .003 |
| 5 | .000 | — | .002 |
| 6 | .007 | — | .006 |
| 7 | .000 | — | .001 |
| 8 | .042 | .1 | .005 |
| 9 | .003 | — | .004 |
| 10 | .030 | .06 | .07 |
| 11 | .020 | .04 | .05 |
| 12 | .020 | .03 | .04 |
| 13 | .025 | .02 | .03 |
| 14 | .037 | .05 | .06 |
| 15 | .007 | — | .01 |
| 16 | .017 | .01 | .02 |
| 17 | .043 | .09 | .10 |
| 18 | .022 | .08 | .09 |
| 19 | .030 | .07 | .08 |

Table II-continued

Comparison of Sensitivity of Microbiological Technique and Technique of the Invention Assay Results

| Sample No. | Known Penicillin Concentration IU/ml | Using Microbiological Technique (IU/ml) | Test Results (per ml) IU |
|---|---|---|---|
| 20 | .000 | — | <.001 |

It should be noted that the foregoing tests consistently detected the presence of as little as 0.01 I.U./ml of penicillin in about 6 minutes of testing time (not including counting time).

It should also be noted that the foregoing procedure involved the simultaneous incubation of both the sample and tagged penicillin for only three minutes and a two minute centrifugation. This test was specifically designed to be acceptably sensitive and as rapid as possible.

Another group of tests were run to demonstrate the sensitivity possible using *B. stearothermophilus*, tagged benzylpenicillin (1500 CPM), and the three minute incubation in a dry bath incubator set at 90° C. The results of this series of tests are set forth in Table III below. The data set forth in table III illustrate that a significant depression in the counts/minute associated with the separated cell fraction occurs when the antibiotic concentration of the sample is raised from zero up through 0.001 I.U./ml, 0.002 I.U./ml, and 0.005 I.U./ml. This test may be conducted, including the counting step, in less than 10 minutes.

Table III

| Sample No. | I.U./ml Pen. G present in sample | Counts/Min. of cells | Average Counts/Min. |
|---|---|---|---|
| 1 | 0 | 365 | |
| | | | 338 |
| 2 | 0 | 311 | |
| 3 | .001 | 207 | |
| | | | 217 |
| 4 | .001 | 227 | |
| 5 | .002 | 191 | |
| | | | 183.5 |
| 6 | .002 | 176 | |
| 7 | .005 | 97 | 100 |
| | | | 100 |

Table III-continued

| Sample No. | I.U./ml Pen. G present in sample | Counts/Min. of cells | Average Counts/Min. |
|---|---|---|---|
| 8 | .005 | 103 | |
| 9 | .010 | 89 | |
| | | | 100.5 |
| 10 | .010 | 112 | |
| 11 | — | 27 | |

EXAMPLE 2

*Bacillus stearothermophilus* was grown in accordance with the procedure set forth in Example 1. The resulting cell suspension is then sonicated to lyse the cells, preferably while the sample is immersed in an ice bath. Unlysed cells are removed by centrifuging the sonicated suspension at 2500 xg for five minutes. The cell membranes containing penicillin binding sites are isolated by centrifugation for 10 minutes at 5000 xg.

One hundred cotton swabs (cotton sections 6.5 g) were then added to 100 ml of a 30 g/l CNBr solution adjusted to pH=11.0 with 5 M NaOH. After 10 minutes, the swabs are removed, rinsed with $NaHCO_3$ solution, and added to the cell membranes produced as set forth above contained in a suspension of $NaHCO_3$ solution pH=8.1. After stirring for 18 hr. at 4° C., the cell membranes are covalently linked to the swabs through the cyanogen bromide. The swabs are then rinsed with distilled water, soaked in ethanolamine for two hours, rinsed again, and dried.

A conjugate of penicillanic acid and peroxidase was prepared as follows. An alkaline solution (pH=9.0) containing 28.1 mg 6 amino penicillanic acid is mixed with a phosphate buffered peroxidase solution containing 8.8 mg peroxidase and 8.2 mg carbodiimide in water. The reaction mixture is maintained at 4° C. for 24 hours while stirring. As a result, the peroxidase and 6 amino penicillanic acid became covalently linked. The conjugate solution is next dialyzed against 0.05 M phosphate buffered saline (PBS); penicillin activity disappears from the PBS after the first change of solution. After four solution changes, the penicillin-peroxidase conjugate is ready for use.

The assay using the reagents prepared as set forth above is conducted by adding a cotton swab to respective test samples (or controls) together with 100 microliters of conjugate solution. The reaction mixture is incubated in a dry well incubator for three minutes at 50° C. During this time, penicillin in the sample (if any) and the peroxidase-tagged penicillanic acid compete for sites of attachment on the cell membranes bonded to the swabs. The sample is then poured from the tube, the swab is washed with water to remove any unbound conjugate, and one ml of a substrate solution is added to the tubes. The substrate solution consists of 1.0 ml 0.3% $H_2O_2$, 25 mg 4 amino antipyrine, and 20 ml phenol dissolved in 50 ml of distilled water.

The swab plus substrate is then incubated at 25° C. If less than 0.05 units of penicillin was present in the sample, sufficient conjugate becomes immobilized on the swab to produce, through the action of the peroxidase, a visually detectable pink to red color in about 15 minutes. If after 15 minutes no color develops, then the sample contained more than 0.05 units penicillin per milliliter.

For more precise results, the optical density of substrate may be read at 510 millimicrons on a spectrophotometer. Results of exemplary tests are set forth below:

| Penicillin conc. | | O.D. (510 mμ) |
|---|---|---|
| 1) | 0.05 units | 0.75 |
| | | 0.78 |
| | 0.00 units | 1.10 |
| | | 1.05 |
| 2) | 0.05 units | 0.70 |
| | | 0.77 |
| | 0.00 units | 1.05 |
| | | 1.00 |
| average O.D. at 0.05 units penn./ml. - 0.75 | | |
| average O.D. at 0.00 units penn./ml. - 1.05 | | |

In view of the foregoing discussion, those skilled in the art will appreciate that it is possible to detect even smaller concentrations of antibiotics by, for example, incubating the sample with the antibiotic sensitive cells for sufficient time to enable all antibiotic present in the sample to attach the receptor sites. The tagged antibiotic would be added thereafter and would attach to any remaining receptor sites. Aside from these modifications, the procedure would be substantially identical to that set forth above and would result in a slightly slower but even more sensitive test.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A process for detecting the presence of an antibiotic in a liquid sample, said process comprising the steps of:

A. incubating the sample with cell parts of a microorganism, sensitive to said antibiotic, said cell parts having receptor sites capable of binding to said antibiotic, said incubation being conducted under conditions to allow antibiotic molecules, if present in the sample, to bind to said receptor sites;

B. incubating the mixture of step A with an enzyme-tagged substance capable of binding with said receptor sites;

C. separating the cell parts from the liquid;

D. determining the amount of enzyme-tagged substance associated either with the separated cell parts or with the liquid; and E. comparing the determination of step D with a standard to obtain an indication of the presence of antibiotic in the sample.

2. The process of claim 1 wherein steps A and B are conducted simultaneously.

3. The process of claim 1 wherein the amount of enzyme-tagged substance associated with the cell parts is determined.

4. The process of claim 1 wherein the antibiotic to be detected is a $\beta$ lactam antibiotic, the enzyme-tagged substance includes a $\beta$ lactam moeity, the microorganism is a $\beta$ lactam antibiotic-sensitive microorganism.

5. The process of claim 4 wherein the microorganism is *Bacillus stearothermophilus*.

6. The process of claim 1 wherein the antibiotic to be detected is a β lactam antibiotic and the enzyme-tagged substance comprises 6-amino pencillanic acid.

7. The process of claim 6 wherein the 6 amino penicillanic acid is tagged with peroxidase.

8. The process of claim 1 wherein said cell parts consist of cell membranes, said membranes are immobilized on an insoluble support, and said separation step is effected by removing said support from the liquid.

9. A process for detecting the presence of a lactam antibiotic in a liquid sample, said process comprising the steps of:
   A. incubating the sample with cell parts immobilized on a water-insoluble support, said cell parts comprising cell membrane of a β lactam antibiotic sensitive microorganism having receptor sites capable of binding to said antibiotic, said incubation being conducted under conditions to allow antibiotic molecules, if present in the sample, to bind to said receptor sites;
   B. incubating the mixture of step A with an enzyme-tagged substance containing the β lactam moiety, said substance being capable of binding with said receptor sites;
   C. removing said support from the liquid;
   D. determining the amount of enzyme-tagged substance associated with said support by incubating said support with an enzyme substrate solution capable of undergoing a detectable chemical change under the catalytic influence of said enzyme; and E. comparing the determination of step D with a standard to obtain an indication of the presence of antibiotic in the sample.

10. The process of claim 9 wherein the enzyme-tagged substance is peroxidase-tagged 6 amino penicillanic acid.

11. The process of claim 10 wherein the enzyme substrate solution includes amino antipyrine and said detectable chemical change is a color change.

12. The process of claim 9 wherein said support is washed after step C.

13. The process of claim 9 wherein said cell parts comprise the cell membranes of *Bacillus stearothermophilus*.

14. A test set for detecting the presence of penicillin antibiotics in a liquid sample such as milk, said set comprising, in combination:
   A. a water insoluble support having cell parts of a penicillin supersensitive microorganism immobilized thereon;
   B. enzyme-tagged 6-amino penicillanic acid;
   C. an enzyme substrate solution capable of undergoing a color change in response to the catalytic influence of the enzyme tag; and
   D. a standard to which the results of tests made with the reagents of A, B, and C may be compared.

15. The test set of claim 14 wherein the cell parts comprise *Bacillus stearothermophilus* cell membranes.

16. The test set of claim 14 wherein the enzyme tag is peroxidase and the substrate solution comprises $H_2O_2$, phenol, and 4 amino antipyrine.

17. The test set of claim 14 wherein the standard comprises an optical density value made under standard conditions, said value corresponding to a selected penicillin antibiotic concentration.

* * * * *

UNITED STATES PATENT AND TRADEMARK OFFICE
CERTIFICATE OF CORRECTION

PATENT NO. : 4,239,852
DATED : December 16, 1980
INVENTOR(S) : Stanley E. Charm

It is certified that error appears in the above-identified patent and that said Letters Patent are hereby corrected as shown below:

Column 1, line 37, change "pesence" to --presence--.

Column 2, line 22, after "than" insert --about--.

Column 3, line 28, change "actinomysin" to --actinomycin--.

Column 3, line 38, change "conenzyme" to --co-enzyme--.

Column 5, line 68, change "bonding" to --binding--.

Column 7, line 50, delete "pO Solution C".

Column 7, between lines 50 and 51, insert --Solution C--.

Column 9, line 9, in the "Sample No." column, insert --1--.

Column 9, line 25, should read --Counts of sample/counts--.

Column 9, line 32, change "samples in" to --samples is--.

Column 10, line 67, under the heading of "Average Counts/Min." in Table III, delete "100" (the penultimate number in the column).

Column 11, line 21, change "cottton" to --cotton--.

UNITED STATES PATENT AND TRADEMARK OFFICE
CERTIFICATE OF CORRECTION

PATENT NO. : 4,239,852
DATED : December 16, 1980
INVENTOR(S) : Stanley E. Charm

It is certified that error appears in the above-identified patent and that said Letters Patent are hereby corrected as shown below:

Column 13, line 3 (claim 6, line 3), change "pencillanic" to --penicillanic--.

Signed and Sealed this

Twenty-third Day of November 1982

[SEAL]

Attest:

GERALD J MOSSINGHOFF

Attesting Officer          Commissioner of Patents and Trademarks